United States Patent [19]

Yahagi et al.

[11] Patent Number: 4,590,498
[45] Date of Patent: May 20, 1986

[54] CHROMOGENIC RECORDING MATERIALS

[75] Inventors: Masakichi Yahagi, Tokyo; Tetsuo Igaki, Kawagoe; Sinzi Yosinaka, Iwatsuki; Kousaku Morita, Saitama; Morikuni Saito, Tokyo; Kimiaki Kinoshita, Kitamoto, all of Japan

[73] Assignee: Shin Nisso Kako Co., Ltd., Japan

[21] Appl. No.: 583,019

[22] Filed: Feb. 23, 1984

[51] Int. Cl.$^4$ .................. B41M 5/16; B41M 5/18; B41M 5/22
[52] U.S. Cl. .................... 346/208; 346/217; 346/221; 427/151
[58] Field of Search ........... 346/216, 217, 221, 225, 346/208, 209; 549/224; 427/151

[56] References Cited

U.S. PATENT DOCUMENTS

| | | | |
|---|---|---|---|
| 2,548,366 | 4/1951 | Green et al. | 346/221 |
| 2,800,458 | 7/1957 | Green | 346/214 |
| 3,681,390 | 8/1972 | Lin | 346/221 |

FOREIGN PATENT DOCUMENTS

| | | | |
|---|---|---|---|
| 6040 | 10/1965 | Japan | 346/200 |
| 4160 | 11/1968 | Japan . | |
| 14039 | 3/1970 | Japan . | |
| 96137 | 2/1973 | Japan | 346/221 |
| 101935 | 4/1973 | Japan | 346/200 |
| 23204 | 7/1976 | Japan . | |
| 56932 | 5/1977 | Japan | 346/221 |
| 34909 | 3/1979 | Japan | 346/221 |
| 10193 | 3/1981 | Japan . | |
| 0178792 | 11/1982 | Japan | 346/221 |
| 0208092 | 12/1983 | Japan | 346/221 |

Primary Examiner—Bruce H. Hess
Attorney, Agent, or Firm—Abelman, Frayne, Rezac & Schwab

[57] ABSTRACT

Chromogenic recording materials which utilizes a fluoran compound of the formula

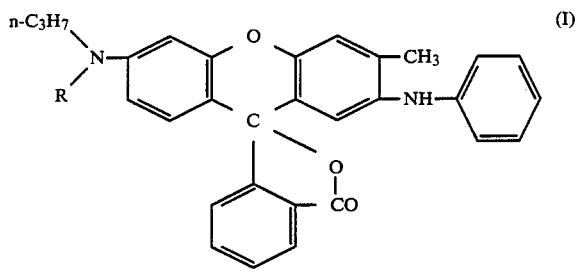

wherein R is methyl or ethyl, is described.

13 Claims, No Drawings

CHROMOGENIC RECORDING MATERIALS

This invention relates to chromogenic recording materials which comprise a fluoran compound of the formula

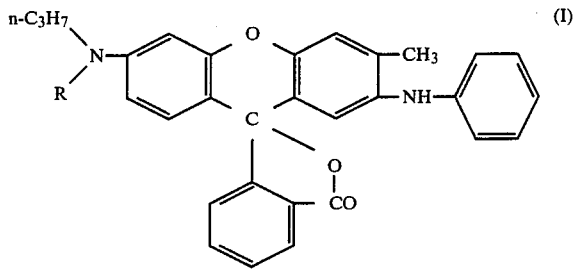

(I)

wherein R represents methyl or ethyl group.

The fluoran compound of the formula (I) according to the invention is by itself substantially colorless substance, but is of a property rapidly producing a color of blackish purple to black by bringing it into intimate contact with an electron accepting material e.g., acid clay, clays, phenol formaldehyde resins, bisphenol A (4,4′-isopropylidene diphenol), benzyl 4-hydroxybenzoate and the like. Because of such property, the fluoran compound is used as a black color-producing chromogenic substance in the chromogenic recording material such as a heat-sensitive recording paper or a pressure-sensitive copying paper.

At the present time, as the black color-producing chromogenic substance in the chromogenic recording material, there have been used extensively two compounds of b 3-diethylamino-6-methyl-7-phenylamino fluoran disclosed in U.S. Pat. No. 3,681,390,

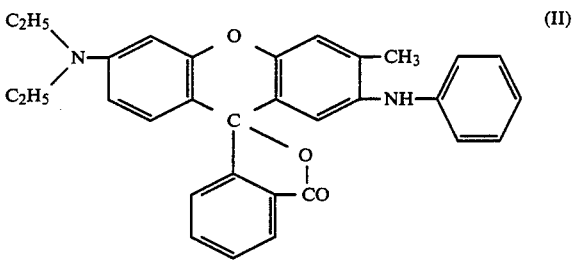

(II)

and 3-N-methylcyclohexylamino-6-methyl-7-phenylamino fluoran disclosed in Japanese Patent Application No. 23204/76

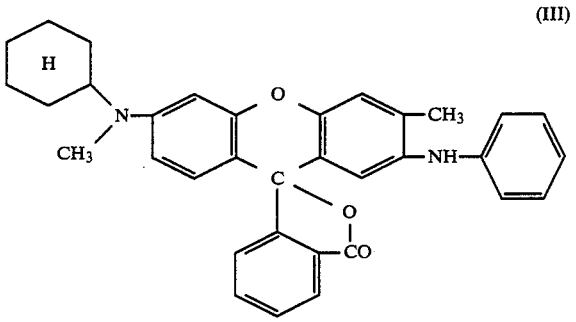

(III)

There is a keen demand to obtain an increased rate of color formation of heat-sensitive recording paper in response to the speed-up of facsimile or the like communication apparatuses. The above two fluoran compounds have not satisfied this demand.

Fluoran compounds of the invention are novel substances which are able to satisfy the above requirements and have the feature that mixtures of the fluoran compounds of the formula (I) and a developer of bisphenol A develop much deeper colores at low temperatures of 90° to 100° C. than similar mixtures of compounds of the formula (II) or formula (III). Moreover, the fluoran compounds of the invention have more excellent black color developability than the compounds of the formula (IV)

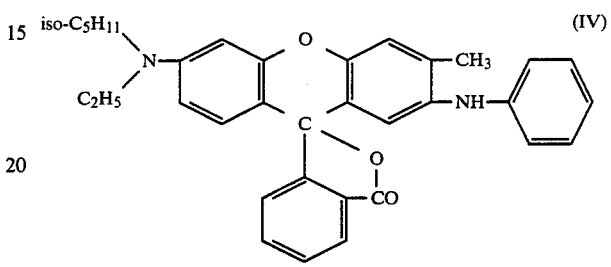

(IV)

The compound of the above formula is disclosed in Japanese Laid-open Patent Application No. 34909/79 as exhibiting a higher level of color formation at low temperatures than known fluoran compounds. These are summarized in Table 1 for comparison.

TABLE 1

| Compound | Color formation temperature (°C.) | | | | | | |
|---|---|---|---|---|---|---|---|
| | 70 | 80 | 90 | 100 | 110 | 120 | 140 |
| A | 0.09 | 0.13 | 0.75 | 1.09 | 1.18 | 1.20 | 1.24 |
| B | 0.09 | 0.13 | 0.71 | 1.07 | 1.17 | 1.20 | 1.25 |
| C | 0.11 | 0.14 | 0.32 | 0.85 | 1.11 | 1.14 | 1.21 |
| D | 0.11 | 0.15 | 0.31 | 0.83 | 1.08 | 1.13 | 1.20 |
| E | 0.10 | 0.13 | 0.61 | 1.01 | 1.16 | 1.19 | 1.23 |

In Table 1, compound A and B are, respectively, compounds of the invention, i.e. 2-N-n-propylmethylamino-6-methyl-7-phenylaminofluoran and 3-N-n-propylethylamino-6-methyl-7-phenylaminofluoran; compound C is a compound of the formula (II), i.e. 3-diethylamino-6-methyl-7-phenylaminofluoran; compound D is a compound of the formula (III), i.e. 3-N-methylcyclohexylamino-6-methyl-7-phenylaminofluoran; and compound E is a compound of the formula (IV), i.e. 3-N-iso-pentylethylamino-6-methyl-7-phenylaminofluoran. In the table, the values indicate color densities, and the respective temperature, of heat-sensitive recording papers made in Examples 1 and 2 and Comparative Example 1. For the color development, heating was effected using Dry Heating Tester (manufactured and sold by Kishino Science Machinery Co., Ltd.) and for the measurement of color density, the Macbeth reflection densitometer was used. Larger values for the color density show deeper hues of color.

Chromogenic substances for heat-sensitive recording paper adapted to use in high speed facsimiles should conveniently be those which develop deep color, under conditions indicated in examples appearing hereinafter, at a temperature below 100° C. The results of Table 1 reveal that the color densities of the fluoran compounds of the present invention are higher at temperatures ranging from about 90° to 100° C. than those of the fluoran compounds for comparison having similar chemical structures (it will be noted that the color densities at 70° and 80° C. and the differences in those density values are of no significance in a practical sense). This means that the fluoran compounds of the invention have favorable color developability for use as chromogenic substances for heat-sensitive recording paper used in high speed facsimiles. As will be noted hereinafter, the color developability can be further enhanced when used in combination with sensitizers.

The fluoran compounds of the invention have not only excellent color developability as discussed above, but also excellent fastenesses to light, cosmetic creams and environments of high temperature and high humidity. Further, heat-sensitive recording papers using these fluoran compounds have prominent features that even immediately after manufacture of the heat-sensitive recording papers or even when preserved over a long term under high temperature and high humidity conditions, they suffer only an extremely small degree of soiling on the chromogenic surface thereof and that coloration of the paper on the chromogenic surface thereof as will be caused upon exposure to sunlight is much smaller in degree than those papers using the known fluoran compounds C, D and E indicated before.

The manner of making heat-sensitive recording papers using the fluoran compounds of the invention is similar to the case where known fluoran compounds are used. For instance, fine particles of a fluoran compound of the present invention and fine particles of a developer are suspended in an aqueous solution of a water-soluble binder. The resulting suspension is applied onto a sheet of paper and dried to obtain a heat-sensitive recording paper with excellent color developability. Addition of a sensitizer to the suspension ensures formation of a heat-sensitive recording paper of very high sensitivity. As a matter of course, the suspension may further comprise fillers, dispersants, antioxidants, desensitizers, anti-tack agents, light stabilizers, fluorescent whitening agents and the like.

The developers used in combination with the fluoran compounds of the invention may include, in addition to BPA and benzyl 4-hydroxybenzoate, bisphenol compounds such as 4,4'-secondary-butylidene bisphenol, 4,4'-cyclohexylidene bisphenol, 2,2'-dihydroxydiphenyl, pentamethylenebis(4-hydroxybenzoate) and the like, 4-hydroxybenzoic esters such as ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate, diphenylmethyl 4-hydroxybenzoate and the like, hydroxysulfones such as 4-hydroxy-4'-methyldiphenylsulfone, 4-hydroxy-4'-isopropoxydiphenylsulfone, 4-hydroxy-4'-hydroxy-4'-butoxydiphenylsulfone and the like, 4-hydroxyphthalic diesters such as dimethyl 4-hydroxyphthalate, dicyclohexyl 4-hydroxyphthalate, diphenyl 4-hydroxyphthalate and the like, hydroxyacetophenone, p-phenylphenol, benzyl 4-hydroxyphenylacetate, p-benzylphenol, hydroquinone monobenzyl ether, and the like.

The water-soluble binders are, for example, polyvinyl alcohol, hydroxyethyl cellulose, carboxymethyl cellulose, styrene-maleic anhydride copolymer, styrenebutadiene copolymer emulsion, vinyl acetate-maleic anhydride copolymer emulsion, polyacrylates, polyacrylamide, starches, casein, gum arabic, and the like.

The sensitizers include, for example, higher fatty acid amides, benzamide, stearic anilide, acetoacetic anilide, thioacetoanilide, dimethyl phthalate, dibenzyl terephthalate, dibenzyl isophthalate, bis(tert-butylphenols), diethers of bisphenol S such as 4,4'-dimethoxydiphenylsulfone, 4-iso-propoxy-4'-n-butoxydiphenylsulfone, 4,4'-di-n-butoxydiphenylsulfone, 4,4'-di-n- or iso-pentyloxydiphenylsulfone and the like, diphenylamine, carbazole, 2,3-di-m-tolylbutane, 4,4'-dimethylbiphenyl, di-beta-naphthylphenylenediamine, and the like.

The fillers are, for example, clay, talc, kaolin, satin white, titanium oxide, calcium carbonate, magnesium carbonate, barium sulfate, magnesium silicate, aluminium silicate, and the like.

The dispersants are, for example, sodium tripolyphosphate, sodium dodecylbenzenesulfonate, sodium salt of lauryl sulfate, metal salts of fatty acids, and the like.

The antioxidants are, for example, 2,2'-methylene-bis(4-methyl-6-tert-butylphenol), 2,2'-methylene-bis(4-ethyl-6-tert-butylphenol), 4,4'-propylmethylene-bis(3-methyl-6-tert-butylphenol), 4,4'-thio-bis(2-tert-butyl-5-methylphenol) and the like.

The de-sensitizers are, for example, stearic acid, zinc stearate, calcium stearate, carnauba wax, paraffin wax, ester wax and the like.

The fluoran compounds of the invention are very excellent as a color-forming dye for heat-sensitive recording paper as described before and may also be excellent when applied to a pressure-sensitive copying paper. For instance, a coated back paper (CB) of pressure-sensitive copying paper prepared in Example 3 assumes a yellowish brown color only in a very slight degree upon exposure of its capsule-coated surface to sunlight. Further, the black color or purplish black color, which appears when a phenolformaldehyde resin coated surface or a clay coated surface of coated front paper (CF) of pressure-sensitive paper is colored with the CB mentioned above respectively, is excellent in light fastness.

The fluoran compounds of the invention are readily soluble in organic solvents such as, for example, alkyl naphthalenes and alkyl diphenyls which are used for the preparation of pressure-sensitive copying paper. This is advantageous in the manufacture of pressure-sensitive copying paper.

The developers used in combination with fluoran compounds of the invention for the manufacture of pressure-sensitive copying paper may be any known ones including, for example, inorganic acidic materials such as terra abla, activated clay, attapulgite, bentonite, colloidal silica, aluminium silicate, magnesium silicate, zinc silicate, tin silicate, calcined clay, talc and the like, aliphatic carboxylic acids such as oxalic acid, maleic acid, tartaric acid, citric acid, succinic acid, stearic acid and the like, aromatic carboxylic acids such as benzoic acid, p-tert-butylbenzoic acid, phthalic acid, gallic acid, salicyclic acid, 3-isopropylsalicyclic acid, 3-phenylsalicyclic acid, 3-cyclohexylsalicyclic acid, 3,5-di-tert-butylsalicyclic acid, 3-methyl-5-benzylsalicyclic acid, 3-phenyl-5-($\alpha,\alpha$-dimethylbenzyl)salicyclic acid, 3,5-di-($\alpha$-methylbenzyl)salicyclic acid, 2-hydroxy-1-benzyl-3-naphthoic acid and the like, salts of the above-indicated aromatic carboxylic acids and metals such as zinc, magnesium, aluminium, titanium and the like, phenolic resins such as p-phenylphenol-formaldehyde resin, p-butylphenol-acetylene resin and the like, and mixtures of these phenolic resins and the metal salts of the aromatic carboxylic acids.

The color formation, upon intimate contact of the present fluoran compound with a developer, also takes place on such substrates other than the aforesaid paper, such as synthetic fiber fabric, non-woven fabric, synthetic paper or synthetic resin sheet (e.g. transparent polyethylene sheet).

The fluoran compounds of the formula (I) are prepared by reacting 1 mole of a benzoic acid derivative represented by the formula (V)

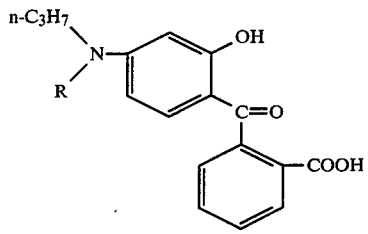 (V)

(in which R has the same meaning as defined before), with about 1 mole of 4-hydroxy- or 4-lower alkoxy-2-methyldiphenylamine represented by the formula

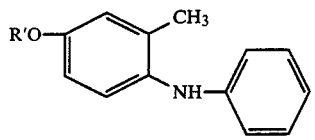

(in which R' represents hydrogen or a lower alkyl group) in concentrated sulfuric acid.

The benzoic acid derivative used in the above reaction is prepared by reacting 1 mole of m-aminophenol derivative of the formula

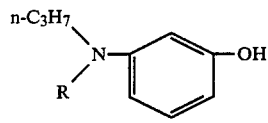

(in which R has the same meaning as defined before) with about 1 mole of phthalic anhydride. This reaction is caused to proceed, for example, by heating both the compounds in a solvent such as toluene, tetrachloroethylene or 1,1,1-trichloroethane. The reaction system is advantageously heated to a refluxing temperature of the solvent used and thus the heating temperature may largely vary depending on the type of solvent and the concentration of the reaction solution. The temperature is generally in the range of 90° to 140° C. The reaction time is greatly influenced by the heating temperature and is ordinarily in the range of 4 to 20 hours. For the reaction, acidic substances including, for example, Lewis acids such as anhydrous zinc chloride may be added as a catalyst.

The m-aminophenol derivatives are obtained, for example, by subjecting m-propylaminophenol obtained by reaction between resorcinol and n-propylamine, to N-alkylation using a suitable methylating or ethylating agent.

Chromogenic recording materials using the fluoran compounds of the invention as a chromogenic substance are, for example, pressure-sensitive copying papers, heat-sensitive recording papers, heat-sensitive copying papers, electro-thermo recording papers, toners for a electrophotography, stamping inks, ribbons for typewriter and the like but are not limited only thereto. For the manufacture of pressure-sensitive copying papers using fluoran compounds of the invention, methods as disclosed in U.S. Pat. Nos. 2,548,366 and 2,800,458 are conveniently used in the practice of the invention. For the heat-sensitive recording materials such as heat-sensitive recording papers or heat-sensitive copying papers, methods as described in Japanese Patent Publication Nos. 6040/65, 4160/68 and 14039/70 can be suitably used. Moreover, toners for electrophotography may be prepared, for example, according to the method as described in Japanese Laid-open Patent Application No. 56932/77. For the electro-thermo recording papers, there are used methods described, for example, in Japanese Laid-open Patent Application Nos. 96137/73 and 101935/73 and also in Japanese Patent Publication No. 10193/81. Upon application, the fluoran compounds of the invention may be used singly or in combination, or may be used in admixture with other chromogenic substances.

Preparation 1 (Preparation of Benzoic Acid Derivatives)

5.7 g of m-N-n-propylmethylaminophenol and 5.6 g of phthalic anhydride were added to 15 ml of toluene, which was heated under reflux while agitating for 7 hours, followed by cooling and adding 50 ml of toluene for dilution. Thereafter, the reaction system was shaked twice with each 70 ml of an aqueous 10% caustic soda solution to extract the resulting benzoic acid derivative as its salt in an aqueous phase. To the extract was added flaky caustic soda until no sodium salt of the benzoic acid derivative was settled and after cooling, the sodium salt was collected by filtration, followed by washing with 50 ml of isopropyl alcohol. The sodium salt was dissolved in 150 ml of water and neutralized with 50% sulfuric acid to a pH of 4 to 5, followed by collecting the resulting crystals by filtration, washing with water and drying to obtain 7.9 g (yield 73.1%) of o-(4-N-n-propylmethylamino-2-hydroxybenzoyl)benzoic acid as white crystals having a melting point of 149° to 151° C.

The above procedure was repeated except that 6.2 g of m-N-n-propylethylaminophenol was used instead of the m-N-n-propylmethylaminophenol, thereby obtaining 7.4 g (yield 65.2%) of o-(4-N-n-propylethylamino-2-hydroxybenzoyl)benzoic acid as white crystals having a melting point of 151.8° to 153° C.

The m-N-n-propylmethylaminophenol and m-N-n-propylethylaminophenol used in the above procedures are oily substances at a normal temperature which are obtained by reacting resorcin and n-propylamine in the presence of anhydrous zinc chloride at a temperature of 180° to 200° C. and alkylating the resulting m-n-propylaminophenol (boiling point 122° to 125° C./0.5 to 1 mmHg), as usual, using a methylating or ethylating agent, respectively.

Preparation 2 (Preparation of Fluoran Compounds)

7.6 g of the o-(4-N-n-propylmethylamino-2-hydroxybenzoyl)benzoic acid prepared in Preparation 1 and 6.1 g of 4-ethoxy-2-methyldiphenylamine were added to 40 g of concentration sulfuric acid, followed by stirring for 48 hours at a temperature of 20° to 25° C. Thereafter, the reaction solution was poured into iced water and the resulting precipitate was collected by filtration. The filter cake was dispersed in water, to which was added an aqueous caustic soda solution to render the dispersion alkaline, followed by filtering, washing the resulting filter cake with water and recrystallizing from toluene to obtain 9.8 g (yield from the benzoic acid derivative 84.5%) of 3-N-n-propylmethylamino-6-methyl-7-phenylaminofluoran as lightly brown fine crystals having a melting point of 175° to 178° C.

The above procedure was repeated except that 8.0 g of o-(4-N-n-propylethylamino-2-hydroxybenzoyl)benzoic acid was used instead of the o-(4-N-n-propylmethylamino-2-hydroxybenzoyl)benzoic acid, thereby obtaining 10.3 g (yield from the benzoic acid derivative 86.4%) of 3-N-n-propylethylamino-6-methyl-7-phenylaminofluoran as lightly pink fine crystals having a melting point of 172° to 174° C.

This invention will now be illustrated by the following examples, but not limited thereto.

EXAMPLE 1

3.5 g of 3-N-n-propylmethylamino-6-methyl-7-phenylaminofluoran, 15.0 g of clay ("UW-90", manufactured and sold by Engelhart Inc. U.S.A.), 41.5 g of a 15% aqueous solution of polyvinyl alcohol (Kuraray Poval, PVA-105, manufactured and sold by Kuraray Co. Ltd., Japan) and 40.0 g of pure water were placed in a 250 ml-capacity polyethylene bottle along with 150 g of glass beads (diameter 1 to 1.5 mm) and sealed. Subsequently, the bottle was placed on a paint conditioner, by Red Devil Co., Ltd., and shaken for 6 hours at 630 vibrations per minute. The glass beads were removed to obtain an aqueous viscous suspension containing particles, having a size of 2 to 3 microns, of 3-N-n-propylmethylamino-6-methyl-7-phenylaminofluoran.

On the other hand, 10.5 g of bisphenol A, 8.0 g of clay (same as above), 41.5 g of a 15% aqueous solution of polyvinyl alcohol (same as above) and 40.0 g of pure water were placed in a 250 ml-capacity polyethylene bottle along with glass beads (diameter 1 to 1.5 mm) and sealed, followed by setting on a paint conditioner of Red Devil Co., Ltd. After shaking of the mixture at 630 vibrations per minute for 10 hours, the glass beads were removed to obtain an aqueous suspension containing particles of bisphenol A having a size of 2 to 3 microns.

To the aqueous bisphenol A suspension was added the aqueous suspension of 3-N-n-propylmethylamino-6-methyl-7-phenylaminofluoran, followed by sufficient agitation for 30 minutes for mixing. The mixture was manually applied onto a white paper by the use of a wire rod No. 12 and dried by hot air of 60° C. for 3 minutes. As a result, there was obtained a very white heat-sensitive recording paper which involved little soils or stains on the surface thereof. This recording paper developed slightly reddish black color very quickly upon heating by application of a heat stylus, heat typing or heat pattern.

This heat-sensitive recording paper was subjected to a color formation test using Dry Heating Tester (manufactured and sold by Kishino Science Machinery Co. Ltd.) by heating the paper on both sides thereof for 5 seconds at temperatures of 70° C., 80° C., 90° C., 100° C., 110° C., 120° C. and 140° C. to permit development of a slightly reddish black color. The color density of the developed side was measured by the Macbeth reflection densitometer RD-514 (Wratten filter #106). The results are shown in Table 1 at the column of compound A.

EXAMPLE 2

The general procedure of Example 1 was repeated using 3-N-n-propylethylamino-6-methyl-7-phenylaminofluoran, instead of 3-N-n-propylmethylamino-6-methyl-7-phenylaminofluoran. There was prepared a heat-sensitive recording paper having a very white coating surface. This paper was developed in the same manner as in Example 1 and the color density of the colored surface was measured with the results shown in Table 1 at the column of compound B.

COMPARATIVE EXAMPLE

The general procedure of Example 1 was repeated using 3-diethylamino-6-methyl-7-phenylaminofluoran, 3-N-cyclohexylmethylamino-6-methyl-7-phenylaminofluoran and 3-N-iso-pentylethylamino-6-methyl-7-phenylaminofluoran, instead of 3-N-propylmethylamino-6-methyl-7-phenylaminofluoran. There were prepared heat-sensitive papers. The papers were subjected to development of color and then to measurement of the color density as described in the Example 1. The color densities of the respective papers are shown in Table 1 at columns of compound C, D and E, respectively. The coating surfaces of these heat-sensitive recording papers were observed to be more soiled than those prepared in Examples 1 and 2.

EXAMPLE 3

1.0 g of 3-N-n-propylmethylamino-6-methyl-7-phenylaminofluoran was dissolved at 90° C. in 20 g of alkylnaphthalene (Solution A). On the other hand, 2.0 g of gelatin (isoelectric point 8.) and 0.5 g of carboxymethyl cellulose were completely dissolved in 120 ml of water (Solution B). The Solutions A and B were mixed together at a temperature of 50° to 60° C. and agitated at a high speed for emulsification, followed by adjusting its pH to 8.5 to 9.0. After the adjustment of the pH, the emulsion was agitated for 20 minutes at high speed and its pH was gradually lowered to 3.8 with dilute acetic acid, followed by cooling to 5° to 10° C. while agitating. Thereafter, 6 g of a formalin solution (37%) was added, followed by continuing agitation for further 1 hour at 10° to 20° C.

Subsequently, the pH of the emulsion was adjusted to 9.0 using a sodium hydroxide solution (5%). The emulsion was further agitated gently for several hours, thereby preparing an emulsion containing very fine capsules each made of a gel film of the carboxymethyl cellulose and gelatin and containing therein an alkylnaphthalene solution of 3-N-n-propylmethylamino-6-methyl-7-phenylaminofluoran. The emulsion was coated onto a sheet of paper and dried to provide a coated back paper (CB) of pressure-sensitive copying paper. On the other hand, a phenol-formaldehyde resin solution was coated onto a sheet paper and dried to provide a coated front paper (CF) of pressure-sensitive paper. The coated surface of the CB was placed on the coated surface of CF. Characters were written on the side of the CB, with the result that black characters appeared very quickly on the coated surface of the CF.

When clay was used instead of the phenol-formaldehyde resin to provide a CF, purplish black characters appeared on the CF.

EXAMPLE 4

The procedure of Example 1 was repeated using benzyl-4-hydroxybenzoate and 4-hydroxy-4'-methyldiphenylsulfone as a developer, instead of bisphenol A. There were prepared heat-sensitive recording papers, respectively.

These papers were developed using the device of Example 1 and developed color densities were measured as described in Example 1. The results are shown in Table 2 below.

TABLE 2

| Developer | Developing temperature (°C.) | | | | | |
|---|---|---|---|---|---|---|
| | 70 | 80 | 90 | 100 | 110 | 120 |
| Benzyl 4-hydroxybenzoate | 0.11 | 0.80 | 1.21 | 1.26 | 1.27 | 1.28 |
| 4-Hydroxy-4'-methyldiphenylsulfone | 0.13 | 0.41 | 0.90 | 1.23 | 1.25 | 1.27 |

EXAMPLE 5

7.0 g of 3-N-n-propylmethylamino-6-methyl-7-phenylaminofluoran, 11.5 g of clay (same as above), 41.5 g of a 15% aqueous solution of polyvinyl alcohol (same as above) and 40.0 g of pure water were treated in the same manner as in Example 1 to prepare an aqueous suspension of the fluoran compound (Solution C).

On the other hand, 7.0 g of dibenzyl terephthalate serving as a sensitizer, 11.5 g of clay (same as above), 41.5 g of a 15% aqueous solution of polyvinyl alcohol (same as above) and 40.0 g of pure water were treated in the same manner as described above, to prepare an aqueous suspension of the dibenzyl terephthalate (Solution D).

Moreover, 10.5 g of bisphenol A, 8.0 g of clay (same as above), 41,5 g of a 15% aqueous solution of polyvinyl alcohol (same as above) and 40.0 g of pure water were treated in the same manner as described above to obtain an aqueous suspension of bisphenol A (Solution E).

Bisphenol A in Solution E was replaced by benzyl 4-hydroxybenzoate and 4-hydroxy-4'-methyldiphenylsulfone, thereby preparing Solutions F and G, respectively.

One part of the Solution C, 1 part of the Solution D and 2 parts of the Solution E were mixed together. One part of the Solution C, 1 part of the Solution D and 2 parts of the Solution F were mixed together. Further, 1 part of the Solution C, 1 part of the Solution D and 2 parts of the Solution G were mixed together. Thus, three coating solutions were prepared.

These solutions were each applied onto a white paper in the same manner as in Example 1 and dried to provide heat-sensitive recording papers E, F and G. These papers were subjected to color development using Dry Heating Tester and their black color densities were measured as described in Example 1. The results are shown in Table 3.

TABLE 3

| Heat-sensitive recording paper | Developer | Developing Temperature (°C.) | | | | | | |
|---|---|---|---|---|---|---|---|---|
| | | 70 | 75 | 80 | 85 | 90 | 95 | 100 |
| E | bisphenol A | 0.13 | 0.49 | 0.74 | 0.97 | 1.10 | 1.14 | 1.20 |
| F | benzyl 4-hydroxy benzoate | 0.43 | 0.85 | 1.17 | 1.20 | 1.22 | 1.25 | 1.28 |
| G | 4-hydroxy-4'-methyl-diphenyl-sulfone | 0.20 | 0.62 | 1.05 | 1.17 | 1.20 | 1.23 | 1.25 |

What we claim is:

1. A chromogenic material which comprises a fluoran compound of the formula

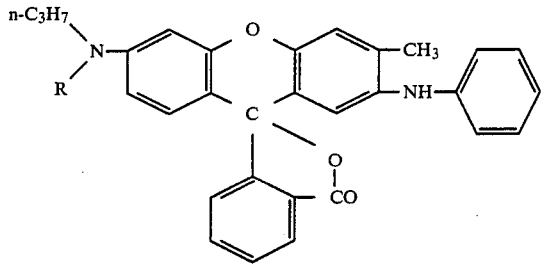

(I)

wherein R represents a methyl or ethyl group, an acidic material capable of causing color formation of said fluoran compound and a substrate which supports the fluoran compound and the acidic substance on its surface.

2. The chromogenic recording material of claim 1 wherein the chromogenic recording material is a heat-sensitive recording paper.

3. The chromogenic recording material of claim 1 wherein the chromogenic recording material is a pressure-sensitive copying paper.

4. The chromogenic recording material of claim 1 comprising bisphenol A as an acidic substance.

5. The chromogenic recording material of claim 1 comprising benzyl 4-hydroxybenzoate as the acidic substance.

6. The chromogenic recording material of claim 1 comprising 4-hydroxy-4'-methyl diphenyl sulfone as the acidic substance.

7. The chromogenic recording material of claim 1 comprising diphenylmethyl 4-hydroxybenzoate as the acidic substance.

8. The chromogenic recording material of claim 1 comprising 4-hydroxy-4'-isopropoxydiphenylsulfone as the acidic substance.

9. The chromogenic recording material of claim 1 comprising 4-hydroxy-4'-n-butoxydiphenylsulfone as the acidic substance.

10. The chromogenic recording material of any one of claims 2, 4, 5, 6, 7, 8 or 9 further comprising dibenzyl terephthalate as a sensitizer.

11. The chromogenic recording material of any one of claims 2, 4, 5, 6, 7, 8 or 9 further comprising dibenzyl isophthalate as a sensitizer.

12. The chromogenic recording material of any one of claims 2, 4, 5, 6, 7, 8 or 9 further comprising 4,4'-di-n-butoxydiphenylsulfone as a sensitizer.

13. The chromogenic recording material of any one of claims 2, 4, 5, 6, 7, 8 or 9 further comprising 4,4'-di-n-pentyloxydiphenylsulfone as a sensitizer.

* * * * *